US012729382B2

(12) United States Patent
Yang et al.

(10) Patent No.: US 12,729,382 B2
(45) Date of Patent: Sep. 8, 2026

(54) TEA PLANT CsVAAT3 GENE AND USE THEREOF

(71) Applicant: Anhui Agricultural University, Hefei (CN)

(72) Inventors: Tianyuan Yang, Hefei (CN); Junjie Wang, Hefei (CN); Xiaojuan Fan, Hefei (CN); Zhaoliang Zhang, Hefei (CN); Xiaohong Lian, Hefei (CN); Xinpeng Zhao, Hefei (CN); Xiaocao Luo, Hefei (CN)

(73) Assignee: Anhui Agricultural University, Hefei (CN)

( * ) Notice: Subject to any disclaimer, the term of this patent is extended or adjusted under 35 U.S.C. 154(b) by 395 days.

(21) Appl. No.: 18/305,944

(22) Filed: Apr. 24, 2023

(65) Prior Publication Data

US 2023/0407318 A1 Dec. 21, 2023

(30) Foreign Application Priority Data

Apr. 24, 2022 (CN) ........................ 202210455505.1

(51) Int. Cl.
*C12N 15/81* (2006.01)
*C12N 1/16* (2026.01)

(52) U.S. Cl.
CPC ............... *C12N 15/81* (2013.01); *C12N 1/16* (2013.01)

(58) Field of Classification Search
CPC ................................. C12N 15/81; C12N 1/16
See application file for complete search history.

(56) References Cited

FOREIGN PATENT DOCUMENTS

| | | | |
|---|---|---|---|
| AU | 2013201664 | B2 | 8/2015 |
| CN | 101445788 | A | 6/2009 |
| CN | 102906267 | A | 1/2013 |
| CN | 113151305 | A | 7/2021 |

OTHER PUBLICATIONS

Addgene pDR196 Sequencing (https://www.addgene.org/browse/sequence/44435/); retrieved Nov. 5, 2025.
Addgene EGFP Sequencing (https://www.addgene.org/browse/sequence/346607/); retrieved Nov. 5, 2025.
Fu et al., "Stable Isotope-Labeled Precursor Tracing Reveals that L-Alanine is Converted to L-Theanine via L-Glutamate not Ethylamine in Tea Plants In Vivo", J. Agric. Food Chem., (2021), vol. 69, pp. 15354-15361.
Feng et al., "Tonoplast-Localized Theanine Transporter CsCAT2 May Mediate Theanine Storage in the Root of Tea Plants (*Camellia sinensis* L.)", Frontiers in Plant Science, (Dec. 2021), vol. 12, Article 797854, (10 pages).
English translation of first Office Action issued in Chinese Patent Application No. 202210455505.1 on Feb. 7, 2023.
English translation of second Office Action issued in Chinese Patent Application No. 202210455505.1 on Mar. 9, 2023.

*Primary Examiner* — Robert A Zeman
(74) *Attorney, Agent, or Firm* — Venable LLP; Keith G. Haddaway

(57) ABSTRACT

The present disclosure provides a tea plant CsVAAT3 gene and use thereof. The tea plant CsVAAT3 gene has a nucleotide sequence shown in SEQ ID NO: 1. A protein coded by the tea plant CsVAAT3 gene has an amino acid sequence shown in SEQ ID NO: 2. An expression pattern of CsVAAT3 in tea plant is significantly positively correlated with the nitrogen level in tea roots. The CsVAAT3 is highly expressed in tea roots. A pDR196-CsVAAT3 plasmid constructed from this gene is transformed into a vacuolar amino acid uptake-deficient yeast strain ypq2, which can restore the growth ability of the yeast mutant on a high-concentration theanine medium. Cloning of the gene is beneficial to analysis of a molecular mechanism of theanine storage in tea roots, providing an important target gene resource and a theoretical basis for cultivation of new tea cultivars with high theanine content.

2 Claims, 4 Drawing Sheets

Specification includes a Sequence Listing.

TEA PLANT CsVAAT3 GENE AND USE THEREOF

CROSS REFERENCE TO RELATED APPLICATION

This patent application claims the benefit and priority of Chinese Patent Application No. 202210455505.1, filed with the China National Intellectual Property Administration on Apr. 24, 2022, the disclosure of which is incorporated by reference herein in its entirety as part of the present application.

SEQUENCE LISTING

The instant application contains a Sequence Listing which has been submitted electronically in XML format and is hereby incorporated by reference in its entirety. The name of the text file containing the sequence listing is HLP20230301382-Sequence listing.xml, has a file size of 22,923 bytes, and was created on Jan. 14, 2026.

TECHNICAL FIELD

The present disclosure relates to the technical field of genetic engineering, in particular to a tea plant CsVAAT3 gene and use thereof.

BACKGROUND

Tea tree (*Camellia sinensis* (L.) O. Kuntze) is an important leaf economic crop. The content of theanine in tea is closely related to the tea quality. However, the vacuolar theanine transporter gene in tea plant has not been identified and the molecular mechanism of theanine storage in root vacuoles is still unclear. The theanine in the tea plant is mainly synthesized in the roots, and the content of theanine in the roots varies with the seasons. When a large amount of theanine is synthesized in tea roots, there is a physiological process of theanine storage in the root cells of the tea plant, and the vacuole is the storage site of many metabolites. Studying the physiological function of the tonoplast theanine transporter gene will help to understand the molecular mechanism of theanine storage, and provide a theoretical basis and target genes for cultivating new quality of high-theanine tea plants.

SUMMARY

An objective of the present disclosure is to provide a tea plant CsVAAT3 gene and use thereof, which can respond to the treatment of different concentrations of nitrogen and can transport theanine into the yeast vacuole in yeast. This provides a new idea for a tea plant to synthesize more theanine, in order to realize the theory and target gene resources of cultivating new tea cultivars with high theanine content.

To achieve the above objective, the present disclosure provides the following technical solutions:

In a first aspect of the present disclosure, a tea plant CsVAAT3 gene is provided, the tea plant CsVAAT3 gene is a tonoplast-localized transporter gene, and the tea plant CsVAAT3 gene has a nucleotide sequence shown in SEQ ID NO: 1 in sequence listing.

Further, the present disclosure further provides a protein sequence encoded by the tea plant CsVAAT3 gene, and the protein sequence is shown in SEQ ID NO: 2 in the sequence listing.

In another aspect of the present disclosure, a tea plant expression vector pDR196-EGFP-CsVAAT3 (DNA sequence: SEQ ID NO: 7) is provided. The expression vector is obtained by digesting a fragment shown in SEQ ID NO: 1 into a pDR196-EGFP vector.

In another aspect of the present disclosure, use of a tea plant CsVAAT3 gene in yeast to transport theanine into a yeast vacuole is provided.

In another aspect of the present disclosure, a method for transporting theanine into a yeast vacuole in yeast is provided, including the following steps:

cloning a tea plant CsVAAT3 gene;

constructing a tea plant expression vector; and transforming the tea plant CsVAAT3 into a yeast mutant.

Further, the tea plant expression vector is pDR196-EGFP-CsVAAT3.

Further, the yeast mutant is a high-concentration theanine-sensitive strain.

Compared with the prior art, the present disclosure has the following beneficial effects:

1) In the present disclosure, an amino acid transporter located on the tonoplast of tea plant is cloned, and functions of the amino acid transporter transporting theanine is verified in yeast, and the expression level of the transporter in tea plant increases with the increase of nitrogen level. The present disclosure further provides recombinant plasmids and transgenic engineered bacteria containing CsVAAT3 gene. The present disclosure enriches the research on tonoplast theanine transporter in tea plants, helps analyze the molecular mechanism of theanine storage in the tea plant, and provides a theoretical basis for cultivating tea plants with higher theanine content.
2) The expression pattern of CsVAAT3 in tea plant is significantly positively correlated with the nitrogen level in tea roots. The CsVAAT3 is highly expressed in tea roots. A pDR196-CsVAAT3 plasmid constructed from this gene is transformed into a vacuolar amino acid uptake-deficient yeast strain ypq2, which can restore the growth ability of the yeast mutant on a high-concentration theanine medium.

DETAILED DESCRIPTION OF THE EMBODIMENTS

Figure 1:
FIG. 1 illustrates expression patterns of CsVAAT3 in different tissues of a tea plant.
Figure 1:
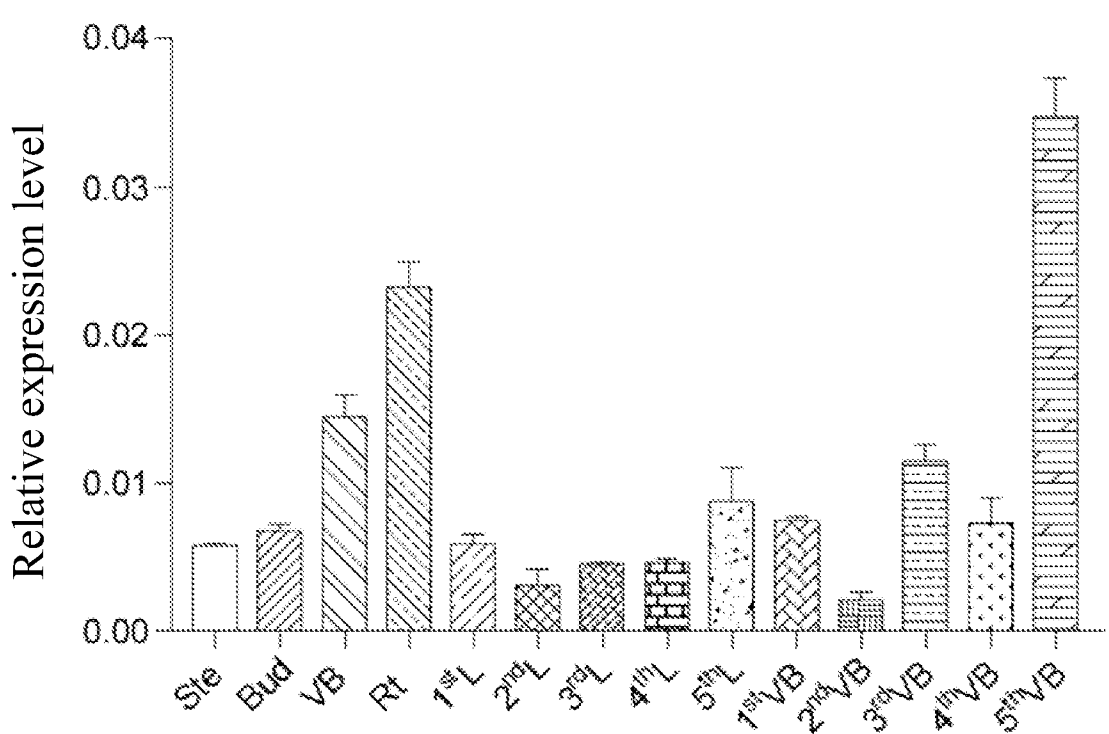

Technical solutions in the example of the present disclosure will be clearly and completely described below with reference to the accompanying drawings in the example of the present disclosure. Apparently, the described example is only a part of, but not all of, the examples of the present disclosure. Based on the example of the present disclosure, all other examples obtained by those of ordinary skill in the art without creative efforts shall fall within the protection scope of the present disclosure.

1. Cloning and Sequence Structure Analysis of CsVAAT3 Gene

The tea plant CsVAAT3 gene is a vacuolar amino acid transporter gene, and cloning and sequence structure analysis thereof are specifically as follows:

The national elite tea cultivar *C. sinensis* cv. Shuchazao was planted in the Agricultural Industrial Park, Anhui Agricultural University, Luyang District, Hefei, Anhui Province, and tender roots were used for RNA extraction. Total RNA extraction was carried out according to the instructions and operations of the RNAprep Pure Plant Kit (Tiangen, Beijing, China), and the RNA content and quality were detected using a spectrophotometer.

The first strand was generated by reverse transcription: with 1 μg of RNA as a template, a reaction buffer was prepared according to the instructions of PrimeScript II 1st Strand cDNA Synthesis Kit (Takara Biotech, China), where 0.6 μL of Oligo dT Primer (50 μM), 0.4 μL of Random 6mers (50 μM), and 1 μL of dNTP Mixture (10 mM each) were added, and the reaction system was made up to 10 μL with RNase Free $ddH_2O$; the RNA was denatured at 65° C. for 5 min and immediately placed on ice. Subsequently, the above reaction buffer was added with 4 μL of 5×PrimerScript Buffer, 0.5 μL of RNase Inhibitor (40 U), and 1 μL of PrimerScript RTase (200 U), made up to 20 μL with $ddH_2O$, and incubated at 42° C. for 45 min, and reverse transcriptase was inactivated at 95° C. for 5 min. After optimization, a quantity of reverse transcription product was taken for subsequent PCR. The CsVAAT3 gene was amplified by conventional PCR using the first-strand cDNA as an RT-PCR template. The upstream primer was 5'-ATGAAGCCATTGAAATTTTCAG-3' (SEQ ID NO: 3), and the downstream primer was 5'-TGATGATACAATAGATTTGAC-3' (SEQ ID NO: 4). The 20 μL PCR system was: 2.5 μL of 10×Ex Taq buffer, 2.0 μL of dNTP, 1.5 μL of $Mg^{2+}$, 1 μL each of upstream and downstream primers, 0.2 μL of Ex Taq, 1 μL of template, and 15.8 μL of $ddH_2O$.

The reaction program was as follows: initial denaturation at 98° C. for 10 s, 35 cycles of denaturation at 98° C. for 10 s, annealing at 57° C. for 30 s, and extension at 72° C. for 2 min; and extension at 72° C. for 10 min. The PCR product CsVAAT3 gene was purified, recovered, and ligated to the pEASY-Blunt Vector (Promega, Shanghai, China) to obtain a pEASY-Blunt::CsVAAT3 plasmid, which was transformed into *Escherichia coli* DH5a Competent Cells and sent to GM for sequencing. The nucleotide sequence of the resulting CsVAAT3 gene is shown in SEQ ID NO: 1 in the sequence listing, which is specifically shown as follows:

```
                                          (SEQ ID NO: 1)
ATGAAGCCATTGAAATTTTCAGACTGTGAAAAAGAGAAGGGTTGTGTTA

AATGGGTTGAGAAGTACTTCAAGGACTGTCTCTGCAACCTCAACGACCA

ACTCTCATTCGGTATTGGTTTAGCAAGTCTGGTTTGTTGGGGTGTTGCT

GAAATCCCTCAAATCATCACCAACTTCCACAACAAGTCCGGCCATGGCC

TGTCTCTCTCATTTCTCTGCACTTGGATTGTTGGTGACATCTTCAACCT

AGTGGGTTGCTTTCTCGAGCCTGCCACGTTGCCGACCCAGTTCTACACT

GCATTGCTATACACAACAATCACAGTAATATTGGTGTTGCAATGCATAT

ATTATGATCACTTTCTCCAATGGTGGAAGCATCGGAACATTCAAGTCAA
```

-continued

```
TCTGGTAAAAGATGAGTCAAAACCTTTGAAATCCGATTATGTCGACTCA

AGTAGAGCTTCAACAAATACCCCTAGTGTTGAAGTACCTAAACGGAGAG

AATTCTATTATACGTCAGCAAGATCATTGGCTAGGAGCAATACGCCACC

ATTCCAATCTTCTTATATTAGGGCTAAAAGTGGTCCTTCTGCTTTGGAG

GTTTACAGTGATTCATCATCTGAAGATGACACAACTCCAGCTCCCTCCA

ACAAGTCCCAGCCTCAGCGAATTCCACGTTCCTTGGGTTATGGAACCTT

CCTGGCTGCCTCAGCCAAATTGCCCATCCAAAGCCGGGCTTTAACAGAA

GAAGCATACATGAAACGATCTGGGATGACATTATTGCAGGAGAATGGAT

TAATGCAAGACTTGGCATGGGGACAATGGTTGGGATGGTTGATGGCAGC

CATATACATGGGCGGTCGAGTCCCACAAATTTGGTTGAATATCAAAAGA

GGGAGTGTGGAGGGCTTGAACCCTTTCATGTTCATCCTTGCCCTCATTG

CCAATGTCACTTACACTGGAAGTATTCTAGTGAGAAGCACTGAATGGGA

GAAGATAAAACCTAACTTGCCTTGGTTGCTGGATGCAGTAGTCTGTGTG

CTGCTTGATCTCTTTATCATCCTTCAGTACGTTTACTACAGGTATTTGA

AGCAAAAGAGGAAGATCGACTCCATTGAAGCATATTATGTAGACCCTGT

GGATGTCAAATCTATTGTATCATCATAA
```

The protein sequence encoded by the CsVAAT3 gene is specifically shown in SEQ ID NO: 2 in the sequence listing:

```
                                          (SEQ ID NO: 2)
MKPLKFSDCEKEKGCVKWVEKYFKDCLCNLNDQLSFGIGLASLVCWGVA

EIPQIITNFHNKSGHGLSLSFLCTWIVGDIFNLVGCFLEPATLPTQFYT

ALLYTTITVILVLQCIYYDHFLQWWKHRNIQVNLVKDESKPLKSDYVDS

SRASTNTPSVEVPKRREFYYTSARSLARSNTPPFQSSYIRAKSGPSALE

VYSDSSSEDDTTPAPSNKSQPQRIPRSLGYGTFLAASAKLPIQSRALTE

EAYMKRSGMTLLQENGLMQDLAWGQWLGWLMAAIYMGGRVPQIWLNIKR

GSVEGLNPFMFILALIANVTYTGSILVRSTEWEKIKPNLPWLLDAVVCV

LLDLFIILQYVYYRYLKQKRKIDSIEAYYVDPVDVKSIVSS
```

2. Differential Expression Analysis of CsVAAT3 Gene (1) Expression of CsVAAT3 Gene in Different Tissues of Tea Plant The national elite tea cultivar *C. sinensis* cv. Shuchazao was planted in the Agricultural Industrial Park, Anhui Agricultural University, Luyang District, Hefei, Anhui Province, and 14 tissues and organs were used to analyze gene expression. The 14 tissues and organs included bud, $1^{st}$ leaf, $1^{st}$ main vein, $2^{nd}$ leaf, $2^{nd}$ main vein, $3^{rd}$ leaf, $3^{rd}$ main vein, $4^{th}$ leaf, $4^{th}$ main vein, $5^{th}$ leaf, $5^{th}$ main vein, vascular bundle, tender stem between $2^{nd}$ and $3^{rd}$ leaves (stem), and root. Also, these samples were used for total RNA extraction and first-strand cDNA synthesis. The reverse transcription product (first-strand cDNA) was diluted 5-fold as a template, and a 10 μL reaction system was prepared using 2×AceQ Universal qPCR SYBR® Master Mix (Vazyme, Nanjing, China): 1.0 μL of 5-fold diluted reverse transcription product, 0.4 μL each of upstream and downstream primers (10 μmol/μL), 5 μL of 2×AceQ Universal qPCR SYBR® Master Mix, and 3.2 μL of $ddH_2O$. Three replicates were prepared for each reaction. Subsequently, the following program was run on the Bio-rad CFX-384 Touch System: i) initial denaturation at 95° C.; ii) 39 cycles of denaturation at 95° C. for 10 s, annealing at 60° C. for 30 s, and extension at 72° C. for 30 s; and iii) from 65° C. to 95° C., to plot the melting curve at 0.1° C./s. The upstream primer was 5'-TCTCTGCAACCTCAACGACC-3' (SEQ ID NO: 8), and the downstream primer was 5'-GCTCGAGAAAGCAACCCACT-3' (SEQ ID NO: 9). With tea plant CsGADPH gene as internal reference, based on the upstream primer (5'-TTGGCATCGTTGAGGGTCT-3', SEQ ID NO: 10) and the downstream primer (5'-CAGTGGGAACACGGAAAGC-3'. SEQ ID NO: 11), the relative expression levels of CsVAAT3 gene in different tissues were calculated through the analysis software of the instrument.

(2) Expression Patterns of CsVAAT3 Gene in Tea Plants at Different Nitrogen Levels Annual tea tree cuttings (*Camellia sinensis* cv. Longjing 43) were taken from the nursery base of Niansheng Agricultural Ecology Co., Ltd., Chaohu City, Anhui Province. Tea seedlings of uniform size were used for hydroponics. In the growth greenhouse of the State Key Laboratory of Tea Tree Biology and Utilization of Anhui Agricultural University, the temperature of the greenhouse was set at 25° C., the light time was 14 h, the dark time was 10 h, the relative humidity was set at 70-75%, and aeration treatment was conducted in the hydroponics process. Tea seedlings were grown in full basal nutrient solution for a month to develop well-developed roots. With a normal nitrogen level as a control, tea seedlings were grown in 0 N, ⅕ N, 1 N, 5 N, and 10 N nutrient solutions. Root tissue samples were collected at different time points (10, 20, and 30 days), and immediately quick-frozen in liquid nitrogen and stored in an ultra-low temperature freezer at −80° C. for analysis of expression levels of CsVAAT3 gene. RNA extraction and quantitative PCR assay were the same as above.

Figure 2:
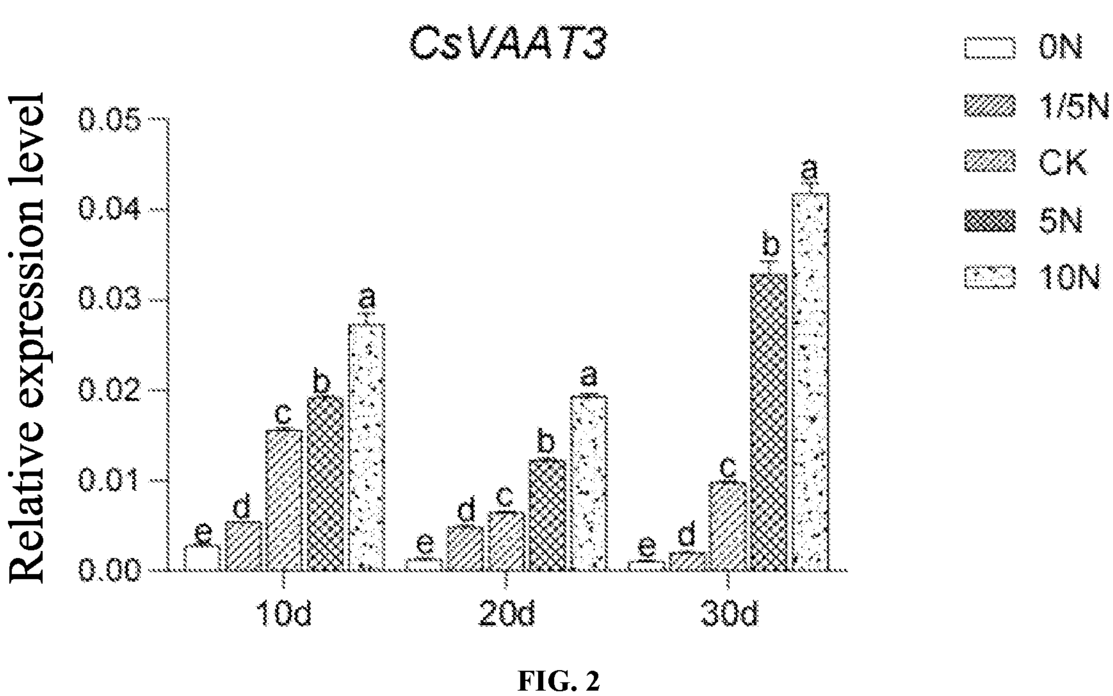
FIG. 2 illustrates expression levels of CsVAAT3 at different nitrogen levels at different time points.

FIGS. 1 and 2 illustrate the expression patterns of tea plant CsVAAT3 in different tissues and under treatment at different nitrogen levels. As can be seen from FIG. 1, the results of qRT-PCR assay showed that CsVAAT3 was expressed in various tissues, but the expression in roots was relatively high; as shown in FIG. 2, under the hydroponic treatment of tea seedlings at different nitrogen levels, the expression levels of CsVAAT3 increased significantly with increasing nitrogen levels, suggesting that CsVAAT3 was able to transport theanine in the tea plant cytoplasm to the vacuole for storage.

3. Subcellular Localization of Tea Plant CsVAAT3

(1) Construction of pDR196-EGFP-CsVAAT3 Vector

With pEASY-Blunt::CsVAAT3 plasmid as a template, based on the upstream primer (5'-CCCCAGCCTCGACTAGTATGAAGCCATTGAAAT-TTTCAG-3', SEQ ID NO: 5) and the downstream primer (5'-AGCTTGATATCGAATTCTGATGATACAATAGAT-TTGAC-3', SEQ ID NO: 6), PCR amplification was conducted. PCR products were recovered with 1.2% agarose gel electrophoresis bands. First, the recovered gene PCR product and the vector plasmid were double digested, and the digested product was recovered with a 1.2% agarose gel electrophoresis band. Using T4 DNA Ligase ligation technology, the band was digested with 2 μL of the vector and 6 μL of the gene, and the product was recovered. 1 μL of T4 DNA Ligase Mix and 1 μL of T4 DNA Ligase Buffer were left to stand overnight at 4° C., transformed into *E. coli* DH5a Competent Cells, and sent to Sangon for sequencing.

(2) Transfection of FM4-64 into Yeast

Yeast mutant YPQ2 is a high-concentration theanine-sensitive strain, and its growth is inhibited in a high-concentration theanine environment, which was used to verify the subcellular localization of the selected gene in yeast. The YPQ2 strain was streaked on YPDA Agar Medium and cultured upside down in a constant temperature incubator at 28° C. for 2-3 days. A well-grown single colony was picked in a 2 mL centrifuge tube, added with 1 mL of YPDA Liquid Medium, and incubated at 28° C. on a shaker at 180 r/min for one day. 200 μL of well-grown yeast suspension was transferred to 30 mL of YPDA Liquid Medium, and incubated on a shaker at 28° C. and 180 r/min for 12-24 h. The yeast suspension was shaken to an OD of 0.8-1.2, 1 mL was pipetted to a 1.5 mL centrifuge tube, the centrifuge tube was centrifuged at 12,000 rpm for 1 min to collect the cells, the supernatant was discarded, and the cells were washed once with sterile water. 5 μL of transformed plasmid DNA was added to the bottom of the tube and pipetted to mix well using a pipette tip. 500 μL of PEG mixture and 5 μL of DTT (1 M, ready for use) were added and vortexed. The centrifuge tube was left to stand at room temperature for 20 min, incubated in water bath at 45° C. for 20 min, and left to stand on ice bath for 20 min. 50 μL of cell pellets were pipetted from the bottom, spread on the SD-U solid medium, and cultivated upside down in a constant temperature incubator at 28° C. for 2-3 days. Positive colonies were verified by yeast colony PCR. The colony PCR program was: denaturation at 98° C. for 10 min; initial denaturation at 94° C. for 5 min; 30 cycles of denaturation at 98° C. for 10 s, annealing at 60° C. for 10 s, and extension at 72° C. for 2 min and 30 s; extension at 72° C. for 10 min, and holding at 16° C. 1 mL of the correctly verified yeast suspension was centrifuged at 6,000 r/min, the supernatant was discarded, the cells were resuspended in Hank's Balanced Salt Solution (HBSS) and stained with 1 μL of FM4-64, and the fluorescence was observed, recorded and photographed under a laser scanning confocal microscope.

Figure 3:
FIG. 3 illustrates the subcellular localization of tea plant CsVAAT3 in yeast.

FIG. 3 illustrates the subcellular localization of CsVAAT3 in yeast. As shown in FIG. 3, GFP represents green fluorescent protein: pDR196-EGFP-CsVAAT3; Bright Field represents a bright field image of pDR196-EGFP-CsVAAT3; and Merged represents a merged image of FM4-64. It can be seen from FIG. 3 that the green fluorescence of CsVAAT3 can be detected on the yeast tonoplast by FM4-64 staining, indicating that the CsVAAT3 protein is localized on the tonoplast.

4. Functional Verification of CsVAAT3 Gene in Yeast (1) Construction of CsCsVAAT3-pDR196 Vector The pEASY-Blunt::CsVAAT3 plasmid was used as a template. The upstream primer was 5'-CCCCAGCCTCGACTAGTATGAAGCCATTGAAAT-TTTCAG-3' (SEQ ID NO: 5) and the downstream primer was 5'-AGCTTGATATCGAATTCTGATGATACAATA-GATTTGAC-3' (SEQ ID NO: 6). PCR products were recovered with 1.2% agarose gel electrophoresis bands. First, the recovered gene PCR product and the vector plasmid were double digested, and the digested product was recovered with a 1.2% agarose gel electrophoresis band. Using T4 DNA Ligase ligation technology, the band was digested with 2 μL of the vector and 6 μL of the gene, and the product was recovered. 1 μL of T4 DNA Ligase Mix and 1 μL of T4 DNA Ligase Buffer were left to stand overnight at 4° C., transformed into *E. coli* DH5a Competent Cells, and sent to Sangon for sequencing.

(2) Transformation of CsVAAT3 into Yeast Mutants

Yeast mutants YPQ2, AVT2, and AVT6 are high-concentration theanine-sensitive strains, and their growth is inhibited in a high-concentration theanine environment, which was used to verify the stress resistance of the selected genes. The YPQ2 strain was streaked on YPDA Agar Medium and cultured upside down in a constant temperature incubator at 28° C. for 2-3 days. A well-grown single colony was picked in a 2 mL centrifuge tube, added with 1 mL of YPDA Liquid Medium, and incubated at 28° C. on a shaker at 180 r/min for one day. 200 μL of well-grown yeast suspension was transferred to 30 mL of YPDA Liquid Medium, and incubated on a shaker at 28° C. and 180 r/min for 12-24 h. The yeast suspension was shaken to an OD of 0.8-1.2, 1 mL was pipetted to a 1.5 mL centrifuge tube, the centrifuge tube was centrifuged at 12,000 rpm for 1 min to collect the cells, the supernatant was discarded, and the cells were washed once with sterile water. 5 μL of transformed plasmid DNA was added to the bottom of the tube and pipetted to mix well using a pipette tip. 500 μL of PEG mixture and 5 μL of DTT (1 M, ready for use) were added and vortexed. The centrifuge tube was left to stand at room temperature for 20 min, incubated in water bath at 45° C. for 20 min, and left to stand on ice bath for 20 min. 50 μL of cell pellets were pipetted from the bottom, spread on the SD-U solid medium (supplemented with 100 mM $K^+$), and cultivated upside down in a constant temperature incubator at 28° C. for 2-3 days. Positive colonies were verified by yeast colony PCR. The colony PCR program was: denaturation at 98° C. for 10 min; initial denaturation at 94° C. for 5 min; 30 cycles of denaturation at 98° C. for 10 s, annealing at 60° C. for 10 s, and extension at 72° C. for 2 min and 30 s; extension at 72° C. for 10 min, and holding at 16° C.

(3) Validation of Tea Plant CsVAAT3 Yeast Dotting Function

A single colony was picked in 20 mL of SD-U solid medium and shaken to an $OD_{600}$ value of about 1.0 at 28° C. and 180 r/min (for about 48 h); 4 mL of yeast suspension was pipetted and centrifuged at 5,000 rpm for 2 min, the supernatant was discarded (under aseptic operation), cells were resuspended with sterile water, and the $OD_{600}$ value was detected; the yeast suspension was diluted with sterile water to an $OD_{600}$ value of 0.6 (the difference between the $OD_{600}$ values of each sample should not exceed 0.02); (under aseptic operation) the yeast suspension was diluted to $10^0$, $10^{-1}$, $10^{-2}$, and $10^{-3}$ in turn. For example, $10^{-1}$ was obtained by pipetting 100 μL from the original yeast suspension (100) to a new 1.5 mL centrifuge tube and mixing well with 900 μL of sterile water; $10^{-2}$ was obtained by pipetting 100 μL from the previous dilution ($10^{-1}$) to a new 1.5 mL centrifuge tube and mixing well with 900 μL of sterile water; $10^{-3}$ was obtained by pipetting 100 μL from the previous dilution ($10^{-2}$) to a new 1.5 mL centrifuge tube and mixing well with 900 μL of sterile water (the whole process was conducted under aseptic operation).

The well-prepared solid medium was placed on the drawn grid line, 2 μL of the yeast suspension was pipetted using a 10 μL pipette, and the yeast suspension was dropped on the intersecting line of the grid. The same yeast suspension of different concentrations was dotted at points in the same horizontal row. Different yeast suspensions of the same concentration were dotted at points in the same column. After the yeast suspension was completely air-dried, the plates were sealed and cultured upside down in a constant temperature incubator at 30° C. Note that the pipette should be perpendicular to the plate when dotting. In general, the yeast growth can be observed after culturing for three days.

Figure 4:
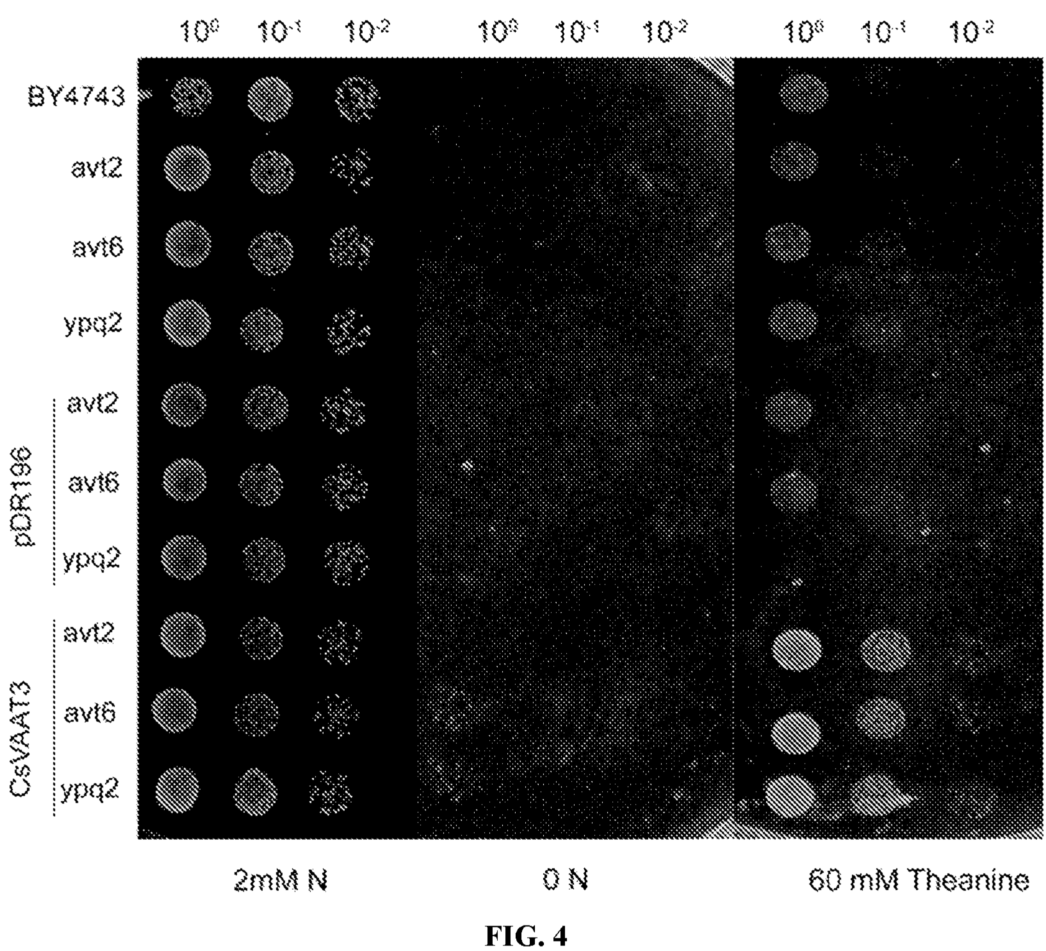
FIG. 4 illustrates the transport of theanine into a vacuole by CsVAAT3 in yeast.

FIG. 4 illustrates the yeast growth phenotype of CsVAAT3 in yeast heterologous system treated with high-concentration theanine. As shown in FIG. 4, the plasmids of the yeast empty vectors pDR196 and pDR196-CsVAAT3 were transformed into high-concentration theanine-sensitive yeast vacuolar amino acid mutants YPQ2, AVT2, and AVT6. Under the treatment of higher theanine (50 mM), the growth of wild-type BY4743 and mutants was significantly inhibited, but the CsVAAT3-transformed yeast mutants were in a normal growth state. It is shown that CsVAAT3 is a functional gene capable of sequestering theanine in the yeast vacuole.

(4) Determination of the Content of Theanine in Yeast Cells and Vacuoles

Wild-type yeast BY4743, mutant YPQ2 and transgenic yeast strains YPQ2-pDR196 and YPQ2-CsVAAT3 were used to determine the content of theanine in whole yeast cells and vacuoles. Single clones of the above strains were picked into 50 mL Erlenmeyer flasks. Three parallel replicates were done for each strain. After shaking to the same $OD_{600}$ at 6,000 r/min for 3 min, the supernatants were discarded. The culture medium without nitrogen source was washed three times, suspended in nitrogen-free medium, and cultured at 28° C. and 200 r/min for 3 h. Subsequently, each shake flask was added with the corresponding concentration of theanine, and cultured at 28° C. and 200 r/min for 3 h. After that, when operating on ice, the $OD_{600}$ of each shake flask was adjusted to the same $OD_{600}$ in nitrogen-free medium. 4 mL of yeast suspension was pipetted into a 5 mL centrifuge tube, centrifuged at 6,000 r/min for 3 min, and washed twice with $ddH_2O$; 3 mL of treatment solution (2.5 mM potassium phosphate, 0.6 M sorbitol, 10 mM glucose, and 200 μM anhydrous cupric chloride) was added to the treatment group, and 3 mL of $ddH_2O$ was added to the control group; each centrifuge tube was left to stand at 30° C. for 15 min, washed with $ddH_2O$ three times, resuspended with 500 μL of $ddH_2O$, boiled at 98° C. for 15 min, and centrifuged at 12,000 r/min for 30 min to collect the supernatant. The theanine content in the solution was detected by HPLC.

Figure 5:
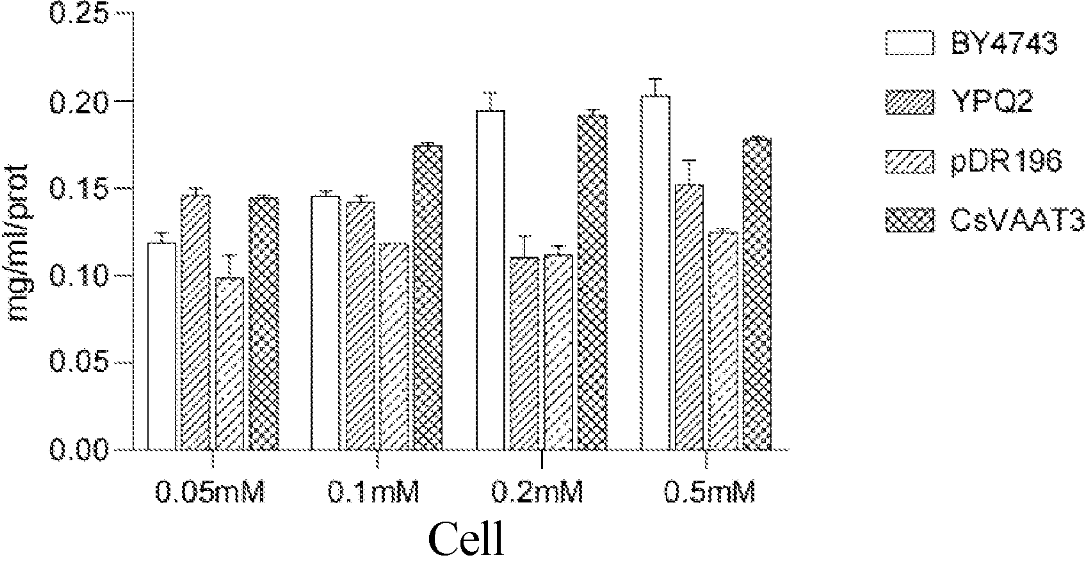
FIG. 5 illustrates intracellular theanine content of different yeast strains.
Figure 6:
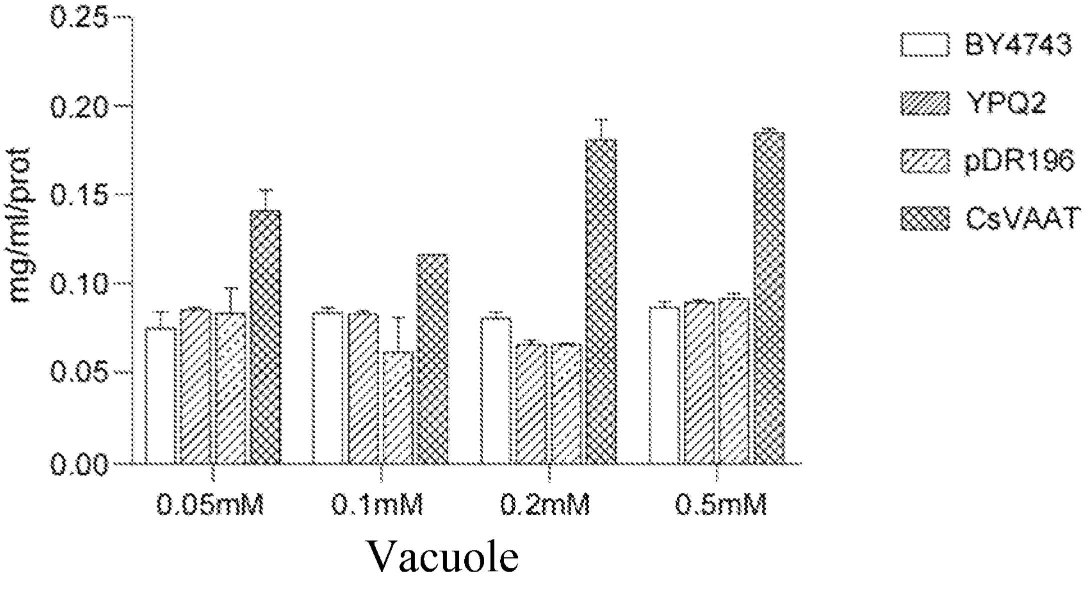
FIG. 6 illustrates the content of theanine in vacuoles of different yeast strains.

FIGS. 5 and 6 illustrate the content of theanine in yeast cells and yeast vacuoles. As shown in FIG. 5, the theanine content in vacuoles of wild-type BY4743 and mutants YPQ2 and YPQ2-pDR196 was significantly lower than that in vacuoles of YPQ2-CsVAAT3 (FIG. 6), and the theanine content in whole cell YPQ2-CsVAAT3 was also significantly higher than that in mutants YPQ2 and YPQ2-pDR196 (FIG. 5). These results indicated that the protein expressed by CsVAAT3 had the function of storing theanine in the yeast vacuole.

The above content is only an example and description of the structure of the present disclosure. Those skilled in the art can make various modifications or supplements to the specific example described or replace them in a similar manner, as long as they do not depart from the structure of the present disclosure or go beyond the scope defined by the claims, all of which fall within the protection scope of the present disclosure.

What is claimed is:

1. A method for transporting theanine into a yeast vacuole in yeast, comprising the following steps:

cloning a tea plant CsVAAT3 gene;

constructing a tea plant expression vector comprising said CsVAAT3 gene; and transforming a yeast mutant with said expression vector; and culturing the yeast mutant in a solid culture medium so that the tea plant CsVAAT3 gene is expressed and theanine is transported into the yeast vacuole;

wherein the tea plant CsVAAT3 gene is a tonoplast-localized transporter gene comprising the nucleotide sequence set forth in SEQ ID NO: 1; and wherein the yeast mutant is selected from the group consisting of yeast mutant YPQ2, yeast mutant AVT2, and yeast mutant AVT6.

2. The method for transporting theanine into a yeast vacuole in yeast according to claim 1, wherein the tea plant expression vector is pDR196-EGFP-CsVAAT3 comprising the nucleotide sequence set forth in SEQ ID NO: 7.

* * * * *

SEQUENCE LISTING

```
Sequence total quantity: 11
SEQ ID NO: 1            moltype = DNA  length = 1155
FEATURE                 Location/Qualifiers
```

```
source                  1..1155
                        mol_type = other DNA
                        note = nucleotide sequence of tea plant CsVAAT3 gene
                        organism = Camellia sinensis
SEQUENCE: 1
atgaagccat tgaaattttc agactgtgaa aaagagaagg gttgtgttaa atgggttgag  60
aagtacttca aggactgtct ctgcaacctc aacgaccaac tctcattcgg tattggttta  120
gcaagtctgg tttgttgggg tgttgctgaa atccctcaaa tcatcaccaa cttccacaac  180
aagtccggcc atggcctgtc tctctcattt ctctgcactt ggattgttgg tgacatcttc  240
aacctagtgg gttgctttct cgagcctgcc acgttgccga cccagttcta cactgcattg  300
ctatacacaa caatcacagt aatattggtg ttgcaatgca tatattatga tcactttctc  360
caatggtgga agcatcggaa cattcaagtc aatctggtaa aagatgagtc aaaacctttg  420
aaatccgatt atgtcgactc aagtagagct tcaacaaata cccctagtgt tgaagtacct  480
aaacggagag aattctatta tacgtcagca agatcattgg ctaggagcaa tacgccacca  540
ttccaatctt cttatattag ggctaaaagt ggtccttctg ctttggaggt ttacagtgat  600
tcatcatctg aagatgacac aactccagct ccctccaaca agtcccagcc tcagcgaatt  660
ccacgttcct tgggttatgg aaccttcctg gctgcctcag ccaaattgcc catccaaagc  720
cgggctttaa cagaagaagc atacatgaaa cgatctggga tgacattatt gcaggagaat  780
ggattaatgc aagacttggc atggggacaa tggttgggat ggttgatggc agccatatac  840
atgggcggtc gagtcccaca aatttggttg aatatcaaaa gagggagtgt ggagggcttg  900
aacccctttca tgttcatcct tgccctcatt gccaatgtca cttacactgg aagtattcta  960
gtgagaagca ctgaatggga gaagataaaa cctaacttgc cttggttgct ggatgcagta  1020
gtctgtgtgc tgcttgatct ctttatcatc cttcagtacg tttactacag gtatttgaag  1080
caaaagagga agatcgactc cattgaagca tattatgtag accctgtgga tgtcaaatct  1140
attgtatcat cataa                                                   1155

SEQ ID NO: 2            moltype = AA  length = 384
FEATURE                 Location/Qualifiers
source                  1..384
                        mol_type = protein
                        note = sequence of protein encoded by the gene of tea plant
                         CsVAAT3
                        organism = Camellia sinensis
SEQUENCE: 2
MKPLKFSDCE KEKGCVKWVE KYFKDCLCNL NDQLSFGIGL ASLVCWGVAE IPQIITNFHN  60
KSGHGLSLSF LCTWIVGDIF NLVGCFLEPA TLPTQFYTAL LYTTITVILV LQCIYYDHFL  120
QWWKHRNIQV NLVKDESKPL KSDYVDSSRA STNTPSVEVP KRREFYYTSA RSLARSNTPP  180
FQSSYIRAKS GPSALEVYSD SSSEDDTTPA PSNKSQPQRI PRSLGYGTFL AASAKLPIQS  240
RALTEEAYMK RSGMTLLQEN GLMQDLAWGQ WLGWLMAAIY MGGRVPQIWL NIKRGSVEGL  300
NPFMFILALI ANVTYTGSIL VRSTEWEKIK PNLPWLLDAV VCVLLDLFII LQYVYYRYLK  360
QKRKIDSIEA YYVDPVDVKS IVSS                                         384

SEQ ID NO: 3            moltype = DNA  length = 22
FEATURE                 Location/Qualifiers
source                  1..22
                        mol_type = other DNA
                        note = upstream primer for PCR amplication of the CsVAAT3
                         gene
                        organism = synthetic construct
SEQUENCE: 3
atgaagccat tgaaattttc ag                                           22

SEQ ID NO: 4            moltype = DNA  length = 21
FEATURE                 Location/Qualifiers
source                  1..21
                        mol_type = other DNA
                        note = downstream primer for PCR amplication of the CsVAAT3
                         gene
                        organism = synthetic construct
SEQUENCE: 4
tgatgataca atagatttga c                                            21

SEQ ID NO: 5            moltype = DNA  length = 39
FEATURE                 Location/Qualifiers
source                  1..39
                        mol_type = other DNA
                        note = upstream primer for construction of
                         pDR196-EGFP-CsVAAT3 Vector
                        organism = synthetic construct
SEQUENCE: 5
ccccagcctc gactagtatg aagccattga aattttcag                         39

SEQ ID NO: 6            moltype = DNA  length = 38
FEATURE                 Location/Qualifiers
source                  1..38
                        mol_type = other DNA
                        note = downstream primer for construction of
                         pDR196-EGFP-CsVAAT3 Vector
                        organism = synthetic construct
```

```
SEQUENCE: 6
agcttgatat cgaattctga tgatacaata gatttgac                          38

SEQ ID NO: 7            moltype = DNA  length = 8251
FEATURE                 Location/Qualifiers
source                  1..8251
                        mol_type = other DNA
                        note = PDR196-EGFP-CSVVAT3
                        organism = synthetic construct
SEQUENCE: 7
ctagtatggt gagcaagggc gaggagctgt tcaccggggt ggtgcccatc ctggtcgagc  60
tggacggcga cgtaaacggc cacaagttca gcgtgtccgg cgagggcgag ggcgatgcca  120
cctacggcaa gctgaccctg aagttcatct gcaccaccgg caagctgccc gtgccctggc  180
ccaccctcgt gaccaccctg acctacggcg tgcagtgctt cagccgctac cccgaccaca  240
tgaagcagca cgacttcttc aagtccgcca tgcccgaagg ctacgtccag gagcgcacca  300
tcttcttcaa ggacgacggc aactacaaga cccgcgccga ggtgaagttc gagggcgaca  360
ccctggtgaa ccgcatcgag ctgaagggca tcgacttcaa ggaggacggc aacatcctgg  420
ggcacaagct ggagtacaac tacaacagcc acaacgtcta tatcatggcc gacaagcaga  480
agaacggcat caaggtgaac ttcaagatcc gccacaacat cgaggacggc agcgtgcagc  540
tcgccgacca ctaccagcag aacaccccca tcggcgacgg ccccgtgctg ctgcccgaca  600
accactacct gagcacccag tccgccctga gcaaagaccc caacgagaag cgcgatcaca  660
tggtcctgct ggagttcgtg accgccgccg ggatcactct cggcatggac gagctgtaca  720
agcccgggct gcaggaattc atgaagccat tgaaattttc agactgtgaa aaagagaagg  780
gttgtgttaa atgggttgag aagtacttca aggactgtct ctgcaacctc aacgaccaac  840
tctcattcgg tattggttta gcaagtctgg tttgttgggg tgttgctgaa atccctcaaa  900
tcatcaccaa cttccacaac aagtccggcc atggcctgtc tctctcattt ctctgcactt  960
ggattgttgg tgacatcttc aacctagtgg gttgcttttct cgagcctgcc acgttgccga  1020
cccagttcta cactgcattg ctatacacaa caatcacagt aatattggtg ttgcaatgca  1080
tatattatga tcactttctc caatggtgga agcatcggaa cattcaagtc aatctggtaa  1140
aagatgagtc aaaacctttg aaatccgatt atgtcgactc aagtagagct tcaacaaata  1200
cccctagtgt tgaagtacct aaacggagag aattctatta tacgtcagca agatcattgg  1260
ctaggagcaa tacgccacca ttccaatctt cttatattag ggctaaaagt ggtccttctg  1320
ctttggaggt ttacagtgat tcatcatctg aagatgacac aactccagct ccctccaaca  1380
agtcccagcc tcagcgaatt ccacgttcct tgggttatgg aaccttcctg gctgcctcag  1440
ccaaattgcc catccaaagc cggctttaa cagaagaagc atacatgaaa cgatctggga  1500
tgacattatt gcaggagaat ggattaatgc aagacttggc atggggacaa tggttgggat  1560
ggttgatggc agccatatac atgggcggtc gagtcccaca aatttggttg aatatcaaaa  1620
gagggagtgt ggagggcttg aaccctttca tgttcatcct tgccctcatt gccaatgtca  1680
cttacactgg aagtattcta gtgagaagca ctgaatggga gaagataaaa cctaacttgc  1740
cttggttgct ggatgcagta gtctgtgtgc tgcttgatct ctttatcatc cttcagtacg  1800
tttactacag gtatttgaag caaaagagga agatcgactc cattgaagca tattatgtag  1860
accctgtgga tgtcaaatct attgtatcat cataagtcga cctcgagggg gggcccggta  1920
cccaattcgc cctatagtga gtcgtattac gcgcggatcc agctttggac ttcttcgcca  1980
gaggtttggt caagtctcca atcaaggttg tcggcttgtc taccttgcca gaaatttacg  2040
aaaagatgga aaagggtcaa atcgttggta gatacgttgt tgacacttct aaataagcga  2100
atttcttatg atttatgatt tttattatta aataagttat aaaaaaaata agtgtataca  2160
aattttaaag tgactcttag gttttaaaac garaattctt attcttgagt aactctttcc  2220
tgtaggtcag gttgctttct caggtatagc atgaggtcgc tcttattgac cacacctcta  2280
ccggcatgcc aattcactgg ccgtcgtttt acaacgtcgt gactgggaaa accctggcgt  2340
tacccaactt aatcgccttg cagcacatcc ccctttcgcc agctggcgta atagcgaaga  2400
ggcccgcacc gatcgccctt cccaacagtt gcgcagcctg aatggcgaat ggcgcctgat  2460
gcggtatttt ctccttacgc atctgtgcgg tatttcacac cgcataatcg gatcgtactt  2520
gttacccatc attgaatttt gaacatccga acctgggagt tttccctgaa acagatagta  2580
tatttgaacc tgtataataa tatatagtct agcgctttac ggaagacaat gtatgtattt  2640
cggttcctgg agaaactatt gcatctattg cataggtaat cttgcacgtc gcatccccgg  2700
ttcattttct gcgtttccat cttgcacttc aatagcatat ctttgttaac gaagcatctg  2760
tgcttcattt tgtagaacaa aaatgcaacg cgagagcgct aatttttcaa acaaagaatc  2820
tgagctgcat ttttacagaa cagaaatgca acgcgaaagc gctattttac caacgaagaa  2880
tctgtgcttc atttttgtaa aacaaaaatg caacgcgaga gcgctaattt ttcaaacaaa  2940
gaatctgagc tgcattttta cagaacagaa atgcaacgcg agagcgctat tttaccaaca  3000
aagaatctat acttcttttt tgttctacaa aaatgcatcc cgagagcgct atttttctaa  3060
caaagcatct tagattactt tttttctcct ttgtgcgctc tataatgcag tctcttgata  3120
actttttgca ctgtaggtcc gttaaggtta gaagaaggct actttggtgt ctattttctc  3180
ttccataaaa aaagcctgac tccacttccc gcgtttactg attactagcg aagctgcggg  3240
tgcatttttt caagataaag gcatccccga ttatattcta taccgatgtg gattgcgcat  3300
actttgtgaa cagaaagtga tagcgttgat gattcttcat tggtcagaaa attatgaacg  3360
gtttcttcta ttttgtctct atatactacg tataggaaat gtttacattt tcgtattgtt  3420
ttcgattcac tctatgaata gttcttacta caattttttt gtctaaagag taatactaga  3480
gataaacata aaaaatgtag aggtcgagtt tagatgcaag ttcaaggagc gaaaggtgga  3540
tgggtaggtt atatagggat atagcacaga gatatatagc aaagagatac ttttgagcaa  3600
tgtttgtgga agcggtattc gcaatatttt agtagctcgt tacagtccgg tgcgtttttg  3660
gtttttgaa agtgcgtctt cagagcgctt ttggttttca aaagcgctct gaagttccta  3720
tactttctag ctagagaata ggaacttcgg aataggaact tcaaagcgtt tccgaaaacg  3780
agcgcttccg aaaatgcaac gcgagctgcg cacatacagc tcactgttca cgtcgcacct  3840
atatctgcgt gttgcctgta tatatatata catgagaaga acggcatagt gcgtgtttat  3900
gcttaaatgc gtacttatat gcgtctattt atgtaggatg aaaggtagtc tagtacctcc  3960
tgtgatatta tcccattcca tgcggggtat cgtatgcttc cttcagcact accctttagc  4020
tgttctatat gctgccactc ctcaattgga ttagtctcat ccttcaatgc tatcatttcc  4080
tttgatattg gatcgatccg atgataagct gtcaaacatg agaattgggt aataactgat  4140
```

-continued

```
ataattaaat tgaagctcta atttgtgagt ttagtataca tgcatttact tataatacag  4200
ttttttagtt ttgctggccg catcttctca aatatgcttc ccagcctgct tttctgtaac  4260
gttcaccctc taccttagca tcccttccct ttgcaaatag tcctcttcca acaataataa  4320
tgtcagatcc tgtagagacc acatcatcca cggttctata ctgttgaccc aatgcgtctc  4380
ccttgtcatc taaacccaca ccgggtgtca taatcaacca atcgtaacct tcatctcttc  4440
cacccatgtc tctttgagca ataaagccga taacaaaatc tttgtcgctc ttcgcaatgt  4500
caacagtacc cttagtatat tctccagtag atagggagcc cttgcatgac aattctgcta  4560
acatcaaaag gcctctaggt tcctttgtta cttcttctgc cgcctgcttc aaaccgctaa  4620
caatacctgg gcccaccaca ccgtgtgcat tcgtaatgtc tgcccattct gctattctgt  4680
atacacccgc agagtactgc aatttgactg tattaccaat gtcagcaaat tttctgtctt  4740
cgaagagtaa aaaattgtac ttggcggata atgcctttag cggcttaact gtgccctcca  4800
tggaaaaatc agtcaagata tccacatgtg tttttagtaa acaaattttg ggacctaatg  4860
cttcaactaa ctccagtaat tccttggtgg tacgaacatc caatgaagca cacaagtttg  4920
tttgcttttc gtgcatgata ttaaatagct tggcagcaac aggactagga tgagtagcag  4980
cacgttcctt atatgtagct ttcgacatga tttatcttcg tttcctgcat gtttttgttc  5040
tgtgcagttg ggttaagaat actgggcaat ttcatgtttc ttcaacacta catatgcgta  5100
tatataccaa tctaagtctg tgctccttcc ttcgttcttc cttctgttcg gagattaccg  5160
aatcaaaaaa atttcaagga aaccgaaatc aaaaaaaaga ataaaaaaaa aatgatgaat  5220
tgaaaagcta attcttgaag acgaaagggc ctcgtgatac gcctattttt ataggttaat  5280
gtcatgataa taatggtttc ttagacgtca ggtggcactt ttcggggaaa tgtgcgcgga  5340
acccctattt gtttattttt ctaaatacat tcaaatatgt atccgctcat gagacaataa  5400
ccctgataaa tgcttcaata atattgaaaa aggaagagta tgagtattca acatttccgt  5460
gtcgccctta ttcccttttt tgcggcattt tgccttcctg tttttgctca cccagaaacg  5520
ctggtgaaag taaaagatgc tgaagatcag ttgggtgcac gagtgggtta catcgaactg  5580
gatctcaaca gcggtaagat ccttgagagt tttcgccccg aagaacgttt tccaatgatg  5640
agcactttta aagttctgct atgtggcgcg gtattatccc gtattgacgc cgggcaagag  5700
caactcggtc gccgcataca ctattctcag aatgacttgg ttgagtactc accagtcaca  5760
gaaaagcatc ttacggatgg catgacagta agagaattat gcagtgctgc cataaccatg  5820
agtgataaca ctgcggccaa cttacttctg acaacgatcg gaggaccgaa ggagctaacc  5880
gcttttttgc acaacatggg ggatcatgta actcgccttg atcgttggga accggagctg  5940
aatgaagcca taccaaacga cgagcgtgac accacgatgc ctgtagcaat ggcaacaacg  6000
ttgcgcaaac tattaactgg cgaactactt actctagctt cccggcaaca attaatagac  6060
tggatggagg cggataaagt tgcaggacca cttctgcgct cggcccttcc ggctggctgg  6120
tttattgctg ataaatctgg agccggtgag cgtgggtctc gcggtatcat tgcagcactg  6180
gggccagatg gtaagccctc ccgtatcgta gttatctaca cgacggggag tcaggcaact  6240
atggatgaac gaaatagaca gatcgctgag ataggtgcct cactgattaa gcattggtaa  6300
ctgtcagacc aagtttactc atatatactt tagattgatt taaaacttca tttttaattt  6360
aaaaggatct aggtgaagat cctttttgat aatctcatga ccaaaatccc ttaacgtgag  6420
ttttcgttcc actgagcgtc agaccccgta gaaaagatca aaggatcttc ttgagatcct  6480
ttttttctgc gcgtaatctg ctgcttgcaa acaaaaaaac caccgctacc agcggtggtt  6540
tgtttgccgg atcaagagct accaactctt tttccgaagg taactggctt cagcagagcg  6600
cagataccaa atactgttct tctagtgtag ccgtagttag gccaccactt caagaactct  6660
gtagcaccgc ctacatacct cgctctgcta atcctgttac cagtggctgc tgccagtggc  6720
gataagtcgt gtcttaccgg gttggactca agacgatagt taccggataa ggcgcagcgg  6780
tcgggctgaa cggggggttc gtgcacacag cccagcttgg agcgaacgac ctacaccgaa  6840
ctgagatacc tacagcgtga gctatgagaa agcgccacgc ttcccgaagg gagaaaggcg  6900
gacaggtatc cggtaagcgg cagggtcgga acaggagagc gcacgaggga gcttccaggg  6960
ggaaacgcct ggtatcttta tagtcctgtc gggtttcgcc acctctgact tgagcgtcga  7020
tttttgtgat gctcgtcagg ggggcggagc ctatggaaaa acgccagcaa cgcggccttt  7080
ttacggttcc tggccttttg ctggcctttt gctcacatgt tctttcctgc gttatcccct  7140
gattctgtgg ataaccgtat taccgccttt gagtgagctg ataccgctcg ccgcagccga  7200
acgaccgagc gcagcgagtc agtgagcgag gaagcggaag agcgcccaat acgcaaaccg  7260
cctctccccg cgcgttggcc gattcattaa tgcagctggc acgacaggtt tcccgactgg  7320
aaagcgggca gtgagcgcaa cgcaattaat gtgagttagc tcactcatta ggcaccccag  7380
gctttacact ttatgcttcc ggctcgtatg ttgtgtggaa ttgtgagcgg ataacaattt  7440
cacacaggaa acagctatga ccatgattac gccaagcttc ctgaaacgga gaaacataaa  7500
caggcattgc tgggatcacc catacatcac tctgttttgc ctgacctttt ccggtaattt  7560
gaaaacaaac ccggtctcga agcggagatc cggcgataat taccgcagaa ataaacccat  7620
acacgagacg tagaaccagc cgcacatggc cggagaaact cctgcgagaa tttcgtaaac  7680
tcgcgcgcat tgcatctgta tttcctaatg cggcacttcc aggcctcgat cgagaccgtt  7740
tatccattgc tttttttgttg tctttttccc tcgttcacag aaagtctgaa gaagctatag  7800
tagaactatg agcttttttt gtttctgttt tccttttttt tttttttacc tctgtggaaa  7860
ttgttactct cacactcttt agttcgtttg tttgttttgt ttattccaat tatgaccggt  7920
gacgaaacgt ggtcgatggt gggtaccgct tatgctcccc tccattagtt tcgattatat  7980
aaaaaggcca aatattgtat tattttcaaa tgtcctatca ttatcgtcta acatctaatt  8040
tctcttaaat tttttctctt tctttcctat aacaccaata gtgaaaatct ttttttcttc  8100
tatatctaca aaaacttttt ttttctatca acctcgttga taaatttttt ctttaacaat  8160
cgttaataat taattaattg gaaaataacc attttttctc tcttttatac acacattcaa  8220
aagaaagaaa aaaaatatac cccagcctcg a                                8251
```

```
SEQ ID NO: 8           moltype = DNA  length = 20
FEATURE                Location/Qualifiers
source                 1..20
                       mol_type = other DNA
                       note = upstream primer for analysis of CsVAAT3 gene
                        expression
                       organism = synthetic construct
SEQUENCE: 8
tctctgcaac ctcaacgacc                                             20
```

-continued

```
SEQ ID NO: 9            moltype = DNA  length = 20
FEATURE                 Location/Qualifiers
source                  1..20
                        mol_type = other DNA
                        note = downstream primer for analysis of CsVAAT3 gene
                         expression
                        organism = synthetic construct
SEQUENCE: 9
gctcgagaaa gcaacccact                                            20

SEQ ID NO: 10           moltype = DNA  length = 19
FEATURE                 Location/Qualifiers
source                  1..19
                        mol_type = other DNA
                        note = upstream primer for analysis of CsVAAT3 gene
                         expression
                        organism = synthetic construct
SEQUENCE: 10
ttggcatcgt tgagggtct                                             19

SEQ ID NO: 11           moltype = DNA  length = 19
FEATURE                 Location/Qualifiers
source                  1..19
                        mol_type = other DNA
                        note = downstream primer for analysis of CsVAAT3 gene
                         expression
                        organism = synthetic construct
SEQUENCE: 11
cagtgggaac acggaaagc                                             19
```